United States Patent
Li et al.

(10) Patent No.: US 7,087,247 B2
(45) Date of Patent: Aug. 8, 2006

(54) POLYESTERS, METHOD FOR PRODUCING SAME, AND DEPOT MEDICAMENTS PRODUCED FROM THESE POLYESTERS

(75) Inventors: Youxin Li, Langenfeld (DE); Detlef Mohr, Biberach (DE); Tim Seiffert, Solingen (DE)

(73) Assignee: Creative Peptide Sweden AB, Stockholm (SE)

( * ) Notice: Subject to any disclaimer, the term of this patent is extended or adjusted under 35 U.S.C. 154(b) by 406 days.

(21) Appl. No.: 10/416,472

(22) PCT Filed: Nov. 8, 2001

(86) PCT No.: PCT/EP01/12888

§ 371 (c)(1),
(2), (4) Date: Nov. 3, 2003

(87) PCT Pub. No.: WO02/38646

PCT Pub. Date: May 16, 2002

(65) Prior Publication Data

US 2004/0072986 A1 Apr. 15, 2004

(30) Foreign Application Priority Data

Nov. 10, 2000 (DE) .......................................... 100 55 742

(51) Int. Cl.
*A61K 9/50* (2006.01)
*C08G 63/08* (2006.01)

(52) U.S. Cl. ........................ 424/499; 424/457; 424/489; 528/354; 528/357; 528/359; 528/361; 264/177.1; 525/54.1; 525/54.2; 525/450; 525/462

(58) Field of Classification Search ................. 528/354, 528/357, 359, 361; 424/487, 489, 499; 264/177.1; 525/54.1, 54.2, 450, 462
See application file for complete search history.

(56) References Cited

U.S. PATENT DOCUMENTS

| | | | |
|---|---|---|---|
| 3,773,919 A | 11/1973 | Boswell et al. | ................ 424/19 |
| 4,526,938 A | 7/1985 | Churchill et al. | ........... 525/415 |
| 5,922,338 A | 7/1999 | Brich et al. | ................. 424/422 |
| 5,929,196 A | 7/1999 | Kissel et al. | ................ 528/271 |

FOREIGN PATENT DOCUMENTS

| | | |
|---|---|---|
| EP | 0 299 730 B1 | 10/1995 |
| EP | 0 407 617 B1 | 5/1997 |
| EP | 0 372 221 B1 | 1/2000 |
| EP | 0 058 481 B2 | 5/2003 |
| WO | WO 87/00011 | 1/1987 |

*Primary Examiner*—Samuel A. Acquah
(74) *Attorney, Agent, or Firm*—Edwards & Angell, LLP; Peter F. Corless; Jeffrey D. Hsi

(57) ABSTRACT

The invention relates to novel absorbable polyesters, produced by ring-opening polymerisation of hydroxycarboxylic acids in the presence of a polyol containing an electrolyte, in an extruder. In particular, the invention relates to novel polylactide glycolide polyesters which are essentially free of dextran sulphate and which are produced by ring-opening polymerisation of lactide and glycolide in the presence of dextran sulphate in the extruder; to the production of the same and to their use in depot medicaments.

28 Claims, 6 Drawing Sheets

Figure 1:
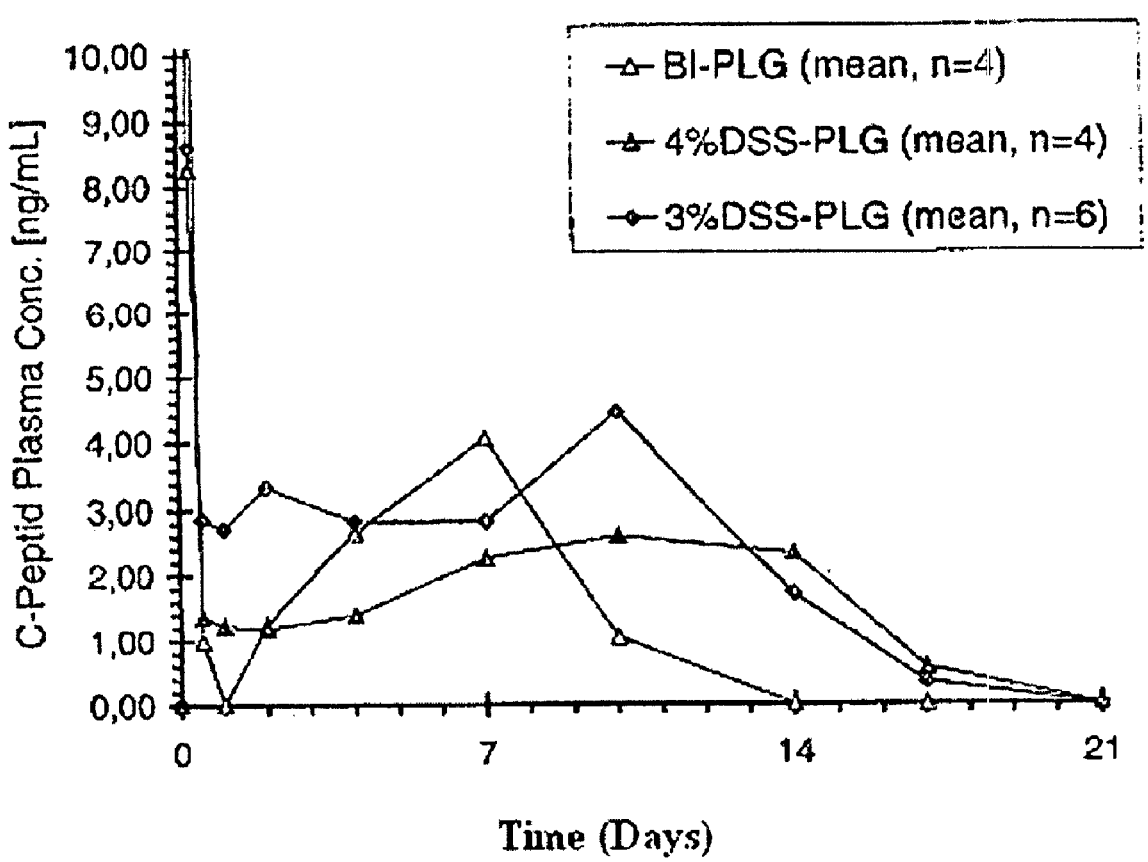
Figure 1:
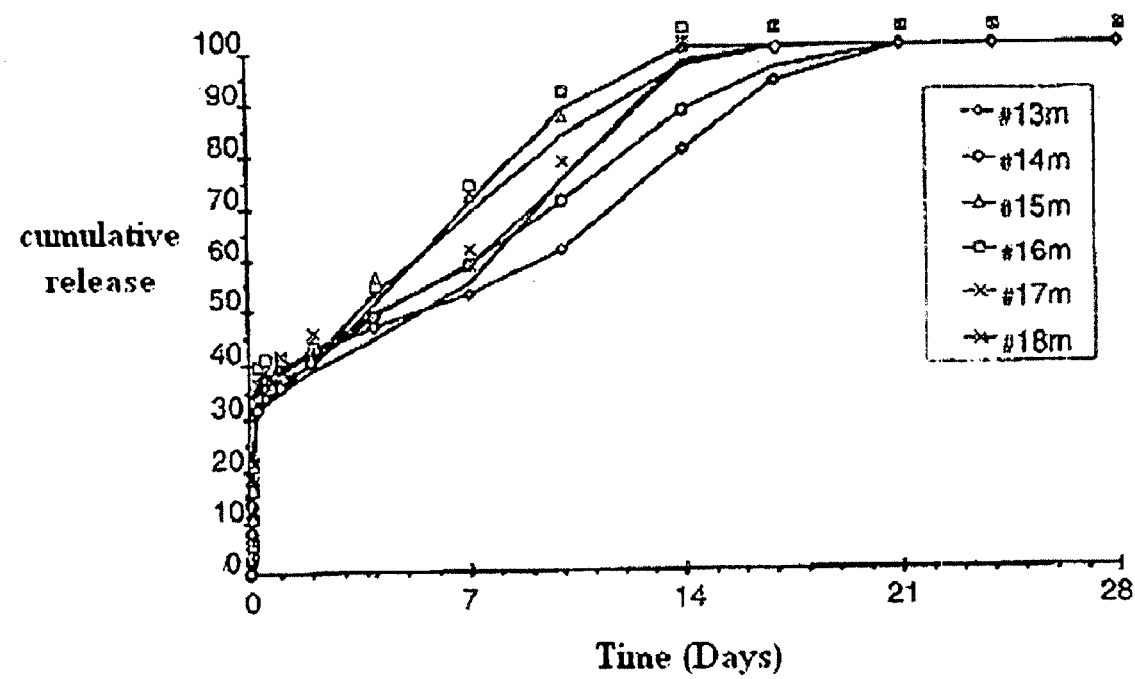
Figure 1:
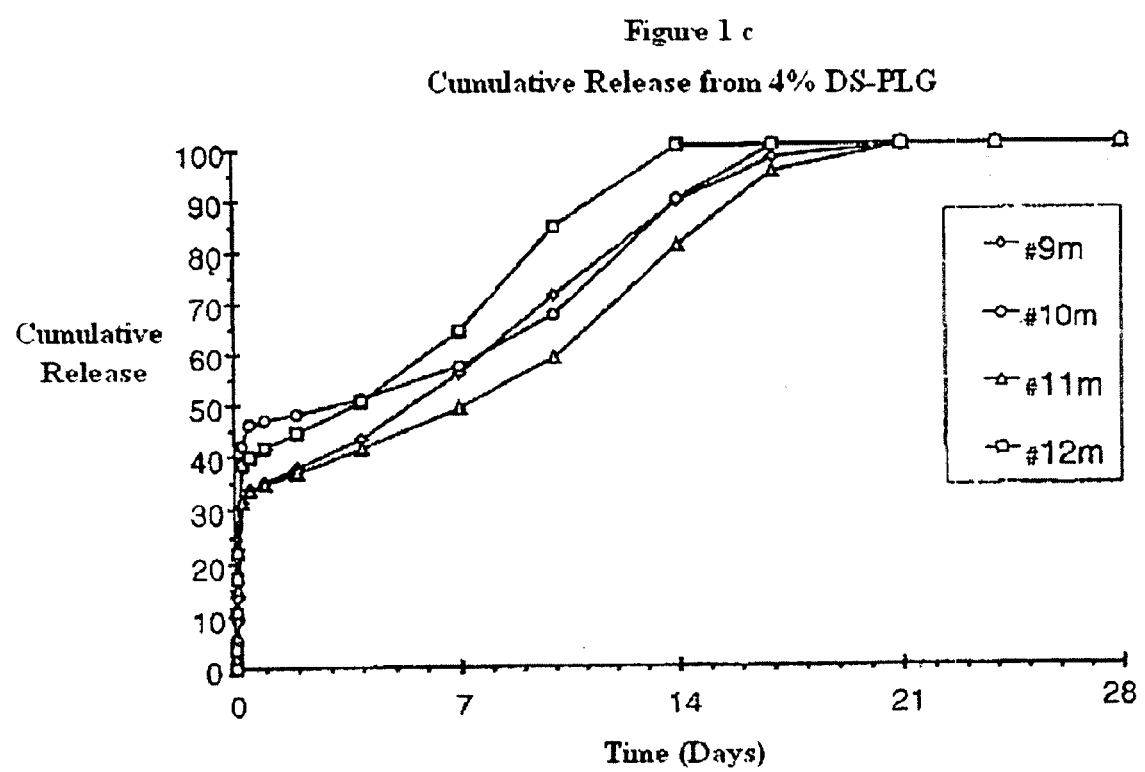
Figure 1:
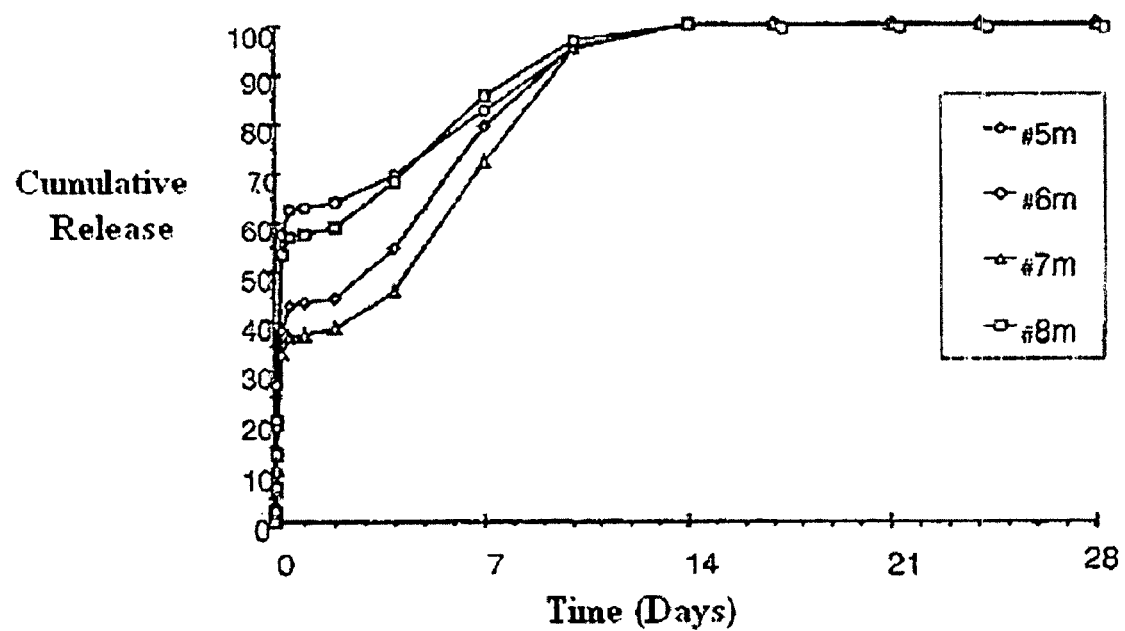

Differential Release of Peptide from different Polymers

Differential Release of Peptide from different Polymers

Cumulative Release from 3% DS-PLG

Cumulative Release from 4% DS-PLG

Cumulative Release from Lactic Acid-Modulated PLG

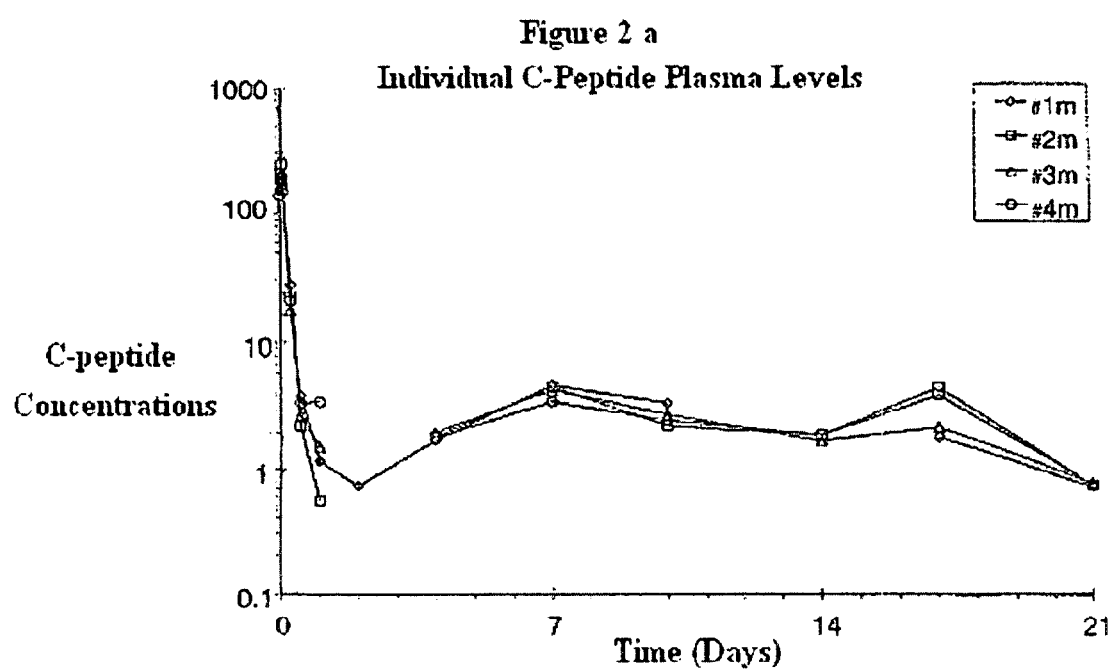

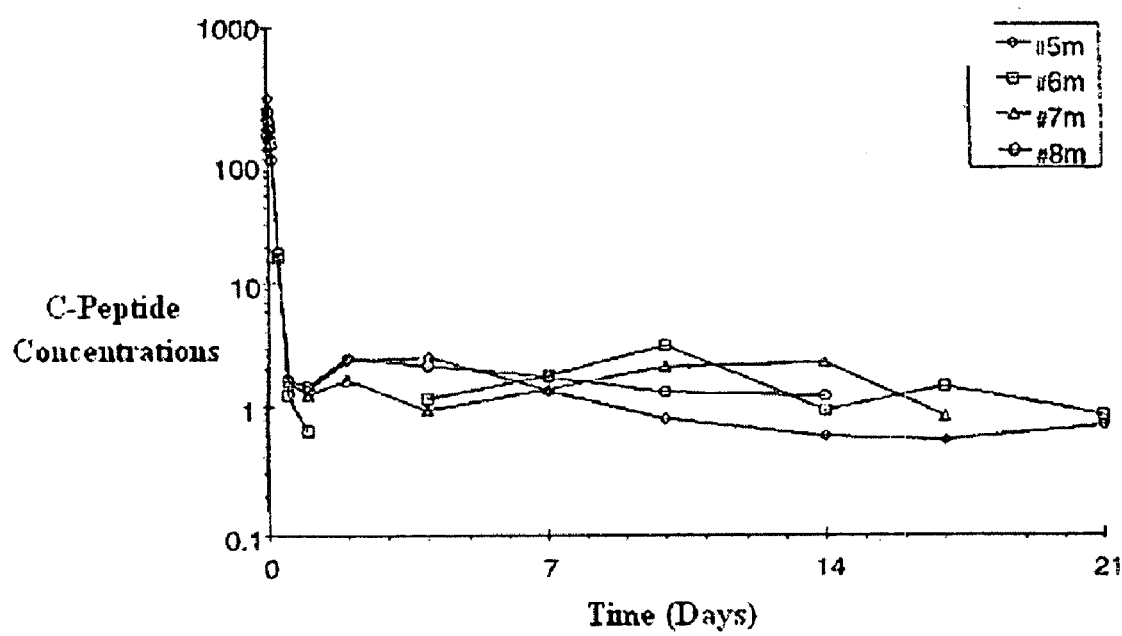

US 7,087,247 B2

POLYESTERS, METHOD FOR PRODUCING SAME, AND DEPOT MEDICAMENTS PRODUCED FROM THESE POLYESTERS

BRIEF DESCRIPTION OF THE INVENTION

This invention relates to novel absorbable polyesters, produced by the ring-opening polymerization of hydroxycarboxylic acids in the presence of an electrolyte-containing polyol in the extruder.

BACKGROUND OF THE INVENTION

For the treatment of chronic illnesses or for continuous substitutive or prophylactic therapy there is a great need for depot formulations capable of releasing a medicine over an extended period of time with therapeutically relevant effectiveness.

These depot formulations can be administered in various ways, for instance orally, topically, inhalationally or parenterally.

For all pharmaceutical agents whose active concentrations should ideally remain uniform over a very long time, parenteral depots such as medicaments suitable for subcutaneous or intramuscular administration are of particular interest. This is all the more important when the pharmaceutically active substance is not adequately absorbed or degraded after enteral administration. These parenteral medications can be formulated for instance as microparticles or implants. Microparticles are of particular interest since because of their small size they permit the use of cannulas and are easily applied.

One major problem in the production of suitable depot formulations and especially of agents having a higher molecular weight such as peptides or proteins lies in the fact that their release often follows a discontinuous or multiphase pattern. To avoid that problem, attempts have been made to control the release profile of peptides. While the production of depot formulations such as microparticles offers only a limited number of possibilities, the properties of the depot formulations can be significantly modulated by modifying the polyesters on which these depot formulations are based.

For the production of suitable depot formulations, biodegradable polymers are of particular interest. Pharmacologically active substances are embedded in these polymer matrices and their release is regulated by the diffusion rate in the polymer as well as the polymer degradation rate. The characteristics of the polymer in terms of the pharmacon release and degradation rate thus determine to a very significant extent the quality of the pharmaceutical depot.

Biodegradable polyesters for embedding active substances on the basis of hydroxycarboxylic acids were described as early as 1973 in U.S. Pat. No. 3,773,919. Particular emphasis was given to polyesters based on lactic acid and glycolic acid, which after their in-vivo application are first hydrolized in nonenzymatic fashion into monomers and are then completely metabolized into $CO_2$ and $H_2O$.

However, the drawback of the polyesters described, when these are used in depot formulations and especially in microparticles, is that there is a strong initial burst of the active ingredient due to the erosion of the surface-bound agent, followed by a phase of severely reduced release, before a release of the agent through the degradation of the bulk of the polyester sets in. Since it is generally desirable for the active substance to be released in as linear a fashion as possible, the polyesters described in U.S. Pat. No. 3,773,919 lend themselves only to a rather minor extent to the production of depot formulations.

Another problem inherent in the polylactide glycolide polyesters (PLG polyesters) described in U.S. Pat. No. 3,773,919 is their slow degradation rate. Polyesters with a high molecular weight, often encountered in the production process, degrade only slowly and can lead to an accumulation of polyester residue as well as to active-substance inclusions in the depots for instance under the skin or in the muscle.

It is therefore particularly important to develop a biodegradable matrix material that can be formulated in a way that in the body it results in a linear release of the active substance over a specified period while at the same time being largely hydrolized.

One possibility to control both the release rate and the degradation rate of the depot concerned is to reduce the molecular weight of the polyester.

EP 058 481 describes the use of a mixture composed of PLG polyesters with different molecular weights. That process, however, results in a very heterogeneous, difficult-to-form polyester mixture that is, at best, only marginally suitable for producing microparticles containing the active substance by spray drying.

EP 299 730 describes the production of a biocompatible polyester by the ring-opening polymerization of D,L-lactide and glycolide, with the chain length controlled by adding lactic acid. Here, however, the depot formulations produced from the resultant PLG polyesters release the active substance in strongly sigmoid fashion, while displaying poor mechanical properties that complicate their processing into microparticles.

EP 407 617 describes the production of a PLG polyester with an elevated hydrolyzing rate by the ring-opening polymerization of D,L-lactide and glycolide. Modulation is accomplished by adding glycosides which in the polymerization reaction are bound to the repetitive glycolide-lactide backbone. While depot formulations based on these polysters are suggested, they are not described.

EP 372 221 describes the continuous production of absorbable polyesters in an extruder. While it suggests the production of polyesters suitable for administering medicaments, it does not disclose such a process. For producing the variously desired viscosity levels it recommends "suitable additives" without, however, providing any indication relative to the nature of these additives.

It has therefore been the objective of this invention to introduce an absorbable polyester that permits a high active-substance content, leads in a pharmaceutical depot formulation to a linear release of the active substance and degrades at a rate in synchronism with the release of the active substance, thus avoiding any accumulation of the polyester in the body.

The invention has further been aimed at solving the upscaling problems associated with the production of absorbable polyesters by batch processing. It is a known fact that results obtained with a more limited synthesizing approach cannot be reproduced in large-volume syntheses, or inadequately at best, due to the thermodynamics involved.

According to the invention, this objective has been achieved by producing absorbable polyesters with the addition in the extruder of electrolyte-containing polyols and, in particular, of dextran sulfate.

ILLUSTRATIONS

The graphs per FIG. 1 represent in-vivo release patterns (in beagles) of micropartides based on DS-modified PLG polyesters or on the commercially available RG 502 PLG polyester, with each of the polyesters loaded with about 7.5% C-peptide. FIG. 1a shows the mean value of the C-peptide plasma concentrations in four (4% DS, RG 502) and, respectively, six (3% DS) dogs. FIGS. 1b–1d show the cumulative quantities of C-peptide released in individual dogs after the administration of 3% DS-PLG (FIG. 1b), 4% DS-PLG (FIG. 1c) and commercially available RG502H (FIG. 1d).

The graphs per FIG. 2 represent in-vivo release patterns (in beagles) of microparticles loaded in each case with about 7.5% C-peptide and with a matrix consisting of DS-modified PLG polyesters. FIG. 2a shows four individual release patterns of 3% DS-modulated polyesters produced with 1200 ppm Sn, FIG. 2b shows the release patterns of 3% DS-modulated polyesters produced with 1600 ppm Sn.

DESCRIPTION OF THE INVENTION

A surprising discovery revealed that the addition of electrolyte-containing polyols, and especially dextran sulfate (DS), in the ring-opening polymerization of hydroxycarboxylic acids and especially of polylactide glycolide leads to new, absorbable polyesters that display a largely linear release pattern over an extended period of time.

Therefore, one object of this invention consists of absorbable polyesters produced by the ring-opening polymerization of hydroxycarboxylic acids in the presence of electrolyte-containing polyols.

For the purpose of this patent application the term "polyester" subsumes homopolymers as well as copolymers resulting from the polymerization of different hydroxycarboxylic acids.

For the purpose of this patent application the term "polymerization" refers to the polymerization of identical monomers such as lactide and to the copolymerization of different monomers such as lactide and glycolide.

For the purpose of this patent application the term "monomers" refers to the unpolymerized constituents of polyesters, meaning that in this case even hydroxycarboxylic acid dimers in lactone form are classified as "monomers".

For the purpose of this patent application the term "hydroxycarboxylic acids" also subsumes dimerous hydroxycarboxylic acids such as lactide and glycolide and hydroxycarboxylic acids in lactone form.

For the purpose of this patent application the term "lactide" includes L-lactide, D-lactide, D,L-lactide and meso-lactide.

For the purpose of this patent application the term "moderator" refers to a substance that is added in the production of an absorbable polyester prior to the polymerization process and modifies the molecular weight and degradation rate of the polyester and thus the release pattern of corresponding formulations without itself acting as a polymerization catalyst and without being embedded in or bonded to the polyester in any substantial quantity.

For the purpose of this patent application the term "substantial quantity" refers to a concentration of more than 200 ppm as related to the total monomer amount.

For the purpose of this patent application the term "formulation" refers to any preparation that encompasses a polymer and at least one pharmacologically active ingredient.

By varying the concentration of the electrolyte-containing polyols in the polymerization mixture it is possible in very simple and practical fashion to modify the molecular weight and the processing characteristics of the polyester but also the degradation rate and the release pattern of the depot formulations based on these polyesters.

Problems are occasionally encountered in the upscaling of the ring-opening polymerization of hydroxycarboxylic acids by the batch process in the presence of electrolyte-containing polyols and especially dextran sulfate. For example, in large batches the temperature is not sufficiently controllable after the addition of a catalyst and dextran sulfate, which leads to inadequate reproducibility.

Another major problem is the uncontrolled, highly exothermal reaction, also in view of the decomposition tendency and explosivity of some electrolyte-containing polyols such as dextran sulfate, so that for safety considerations a batch-mode production process requires a greater investment in equipment.

In contrast thereto, the inventors were surprised to find that ring-opening polymerization of hydroxycarboxylic acids and especially polylactide glycolide in the presence of electrolyte-containing polyols in an extruder reproducibly and safely results in the polyesters per this invention with excellent processing and release characteristics.

Extruders such as dual-screw extruding machines have been employed in prior art and are widely used in the industry for homogenizing granulated materials. The extruder used in producing the polyesters per this invention is equipped with feed systems through which the monomers or monomer mixtures, the modulator, the polymerization catalyst and any adjuvants can be introduced. The polymerization mixture is fed along the longitudinal axis of the extruder, moving past one or several separately controllable heating elements by means of which a precisely controllable temperature profile is obtained. The first thermal element of the extruder also contains cooling provisions needed to prevent an excessive initial heating of the reaction mixture.

Performing the polymerization with a forced flow of the polymerization mixture with a predefined temperature profile permits a continuous process with precisely reproducible parameters, offering substantial advantages over a discontinuous batch process in which, when upscaled, reproducibility is very difficult to attain.

With regard to the addition of electrolyte-containing polyols and especially of DS, using the extruder also permits safe production of the polyester per the invention given the fact that, contrary to the batch process, only small amounts of the substance are introduced. Accordingly, in contrast to the batch process, there is no strong initial temperature build-up. Besides, the venting sections of the extruder ensure adequate pressure relief.

One object of this invention is therefore constituted of a polyester produced by ring-opening polymerization of hydroxycarboxylic acids in lactone form in the presence of an electrolyte-containing polyol in the extruder. In this patent application, these polyesters are also referred to as "polyol-modulated polyesters".

Suitable hydroxycarboxylic acids include lactide, glycolide, methyl glycolide, dimethyl glycolide, diethyl glycolide, dibutyl glycolide, caprolactone, valerolactone, propiolactone, butyrolactone and pivalolactone.

Highly preferred are polyesters produced by the ring-opening polymerization of lactide and glycolide in the presence of an electrolyte-containing polyol in the extruder. For the purpose of this patent application these polyesters are also referred to as "polyol-modulated PLG polyesters".

Particularly preferred are polyesters produced by the ring-opening polymerization of lactide and glycolide in the presence of DS in the extruder. For the purpose of this patent application these polyesters are also referred to as "DS-modulated PLG polyesters" or "DS-PLG polyesters".

In the polyesters according to the invention, the electrolyte-containing polyol is incorporated either not at all or in minute quantities only. Consequently, after their production in the extruder with the addition of DS the polyesters routinely have a sulfur content below the detection limit of 5–10 ppm, and at less than 200 ppm even the carbohydrate content is unexpectedly low. It follows that, if any at all, very few secondary fractions of the polyester are sulfate- or carbohydrate-modified.

Compared to prior-art PLG polyesters (such as the commercially available RG502H and RG503H polyesters made by Boehringer Ingelheim), the DS-modulated PLG polyesters produced by the method according to this invention, having the same molecular weight, display a significantly improved release pattern and thus superior properties (see implementation example #6, FIGS. 1–2). One reason derives from the particularly controllable, continuous process conditions in the extruder, another reason is the effect of the electrolyte-containing polyol.

Without wanting to be tied to any particular theory it can be assumed that, apart from the main fraction that consists of chemically unmodified hydroxycarboxylic acid structures, there additionally exist trace components of slightly modified polyesters that do not permit direct analytical characterization yet influence the pattern of the overall fraction.

Electrolyte-containing polyols, and especially dextran sulfate, can therefore be viewed as moderators of the production process according to this invention.

Thus, a preferred object of the invention is a polyester produced by the ring-opening polymerization of hydroxycarboxylic acids in lactone form in the presence of an electrolyte-containing polyol in the extruder, said polyester containing hydroxycarboxylic acid units that are essentially free of electrolyte-containing polyols.

Highly preferred according to the invention are polyol-modulated PLG polyesters composed of lactide and glycolide units that are essentially free of electrolyte-containing polyols.

For the purpose of this patent application the expression "essentially free of electrolyte-containing polyols" signifies that the electrolyte-containing polyol, added as a moderator, is incorporated in the polyester at a concentration of 200 ppm maximum.

Suitable electrolyte substitutes for the moderator include for instance sulfates, phosphates, carboxyl groups or amino groups bound to polyols.

The polyol constituent of the moderator may be composed of identical or different mutually linked units, displaying a linear or cyclic structure. Examples thereof include polymers or oligomers from carbohydrates such as inulins, dextrans, xylans, cyclodextrins as well as hydroxy-group-substituted polyesters such as polyvinyl alcohol (PVA), and finally copolymers from PVA for instance with acrylic acid.

Electrolyte-containing polyols preferred as moderators include dextran sulfate, diethylaminoethyl dextran, xylan sulfate, cyclodextrin sulfate and partially sulfated PVA, with dextran sulfate (DS) given particular preference.

Dextran sulfates with a high (MG 500 kDa) or medium (8–30 kDa) molecular weight are equally suitable for the purpose. Preference is given to a DS with a molecular weight of less than 40 kDa and ideally with a MG of 10–30 kDa.

The preferred concentration ranges for electrolyte-containing polyols such as dextran sulfate are 1–10%, especially 1–6% and ideally 3–5% as related to the total amount of the monomers used.

As shown in Table 1, varying the amount of electrolyte-containing polyol in the polymerization mixture of the extruder, with all other process conditions remaining unchanged, permits altogether easy control of the molecular weight and the inherent viscosity of the polyesters according to this invention: As the concentration of the added DS is increased, the mean molecular weight and the inherent viscosity will decrease.

TABLE 1

| DS Amount | Lot Number | Inherent Viscosity (ChCl3) | Molec. Weight | Sn (II) |
|---|---|---|---|---|
| 2% | RES-0085 | 0.38 dl/g | 28.8 kDa | 1200 ppm |
| 3% | RES-0106 | 0.30 dl/g | 21.1 kDa | 1200 ppm |
| 4% | RES-0083 | 0.24 dl/g | 14.3 kDa | 1200 ppm |

Preferred, according to the invention, are polyol-modulated PLG polyesters with an average molecular weight of 7–40 kDa, and better yet 10–30 kDa, since these PLG polyesters lend themselves particularly well to the production of depot formulations and especially to the production of microparticles, displaying a highly desirable release pattern.

For the purpose of this patent application the term "average or mean molecular weight" of a polyester is a molecular weight (MW) determined in a GPC analysis under utilization of polystyrene standards for the calibration, with tetrahydrofuran serving as the eluent.

In a preferred form of implementation of the invention, a 0.1% solution of the DS-modulated PLG polyester per the invention in chloroform at 25° C. has an inherent viscosity of 0.2–0.45 dl/g and a molecular weight of 10–30 kDa.

Compared to the prior-art PLG polyesters produced with lactic acid as the modulator, the DS-modulated PLG polyesters according to the invention display a more rapid degradation rate that is better matched with the desired release pattern of the active substance. They also allow for the prevention of a polyester accumulation.

In general, the initial active-substance burst is significantly reduced and the phase of considerably lower active-agent release following the burst is substantially shorted or eliminated (ref. FIG. 1). At the same time, the overall duration of the release is extended, permitting a continuous in-vivo release of the active substance over a period of 2–3 weeks (ref. FIGS. 1–2).

The PLG polyesters per this invention are soluble in various organic solvents such as benzene, acetone and chloroform. The average block length of the PLG polyesters, modulated according to the invention, is between 2.5 and 4, the glass transition temperature is about 40° C.

As a major advantage, it is possible to establish in the extruder a continuous process with a defined thermodynamic profile, superbly suited to the large-scale production of the polyesters per the invention. Varying temperatures can be preset for different zones of the extruder, permitting the creation of a precisely defined temperature profile. It has been found that polymerization temperatures of 170–220° C. and especially 170–200° C. are ideal for the production of the polyester according to the invention.

Suitable catalysts for the ring-opening polymerization of hydroxycarboxylic acids include tin, titanium or aluminum compounds, with particular preference given to tin (II) compounds such as tin (II) oxide and especially tin (II) octoate.

The catalyst concentrations preferred for producing polyesters per the invention range in excess of 1000 ppm, especially 1000–2000 ppm and ideally 1200–1600 ppm as related to the total quantity of the monomers used. Catalysts if added in concentrations of less than 600 ppm would render the polyesters per this invention less soluble in organic solvents, making their processing more difficult.

Since the use of high catalyst concentrations is not without some toxicological hazards, the metal-ion concentration of the polyester is preferably depleted upon completion of the polymerization.

A preferred object of this invention is therefore constituted of a polyester produced by the ring-opening polymerization of hydroxycarboxylic acids in the presence of an electrolyte-containing polyol in the extruder, where tin (II) serves as the polymerization catalyst and the tin (II) content in the polyester is then depleted to below 30 ppm and preferably below 20 ppm.

Table 2 summarizes the major differences between the prior-art lactic-acid-modulated PLG polyesters and the DS-modulated PLG polyesters of this invention:

TABLE 2

|  | Lactic-Acid-Modulated Polyesters | DS-Modulated Polyesters |
| --- | --- | --- |
| Peptide release | Sigmoid over a maximum of 14 days | Linear over 20–30 days |
| Degradation | Slow | Rapid |
| Hydrophilic capacity | Low | High |
| Catalyst amount | Up to 600 ppm | Preferably over 1000 ppm |

Another object of this invention is constituted of methods for producing the absorbable polyesters according to the invention.

One object of the invention is the production of absorbable polyesters by the ring-opening polymerization of hydroxycarboxylic acids in the extruder, characterized in that electrolyte-containing polyols serving as moderators are added to the polymerization mixture.

The electrolyte-containing polyol is preferably added before the addition of the catalyst. The moderator can be placed in the extruder, or mixed with one or several monomers and jointly introduced in the extruder, or added to the preinserted and premixed monomers in the extruder. All these procedural variations are parts and objects of the invention and are subsumed in this patent application by the expression "an electrolyte-containing polyol/a moderator is added to the polymerization mixture".

In a preferred form of implementation the invention encompasses a method for producing absorbable polyesters by ring-opening polymerization in the extruder, in which process the monomers used are lactide and/or glycolide and DS is added as the moderator.

As mentioned further above, the inventors were surprised to find that in the ring-opening polymerization of hydroxycarboxylic acids it is particularly advantageous to use large catalytic quantities. When higher amounts of catalyst are added, the release pattern and processability of the resulting polyesters are better.

Another object of this invention is therefore constituted of a method for producing polyhydroxycarboxylic acids by means of ring-opening polymerization in the extruder, characterized in that the catalyst added to the monomer mixture consist of at least 1000 ppm Sn (II), preferably 1000–2000 ppm Sn (II) and ideally 1200–1600 ppm Sn (II) as related to the amount of the monomers used.

The method can also encompass the removal of the catalyst. Corresponding purification methods have been established in prior art. For example, EP 270 987 describes the removal of catalysts from polymers by treating the polymers with acids or EDTA in diphasic systems.

Alternatively, the catalyst can be removed in a monophasic system by separating the polymer from the solvent after acids have been added. Preferred means for separating the catalyst include carboxylic acids such as acetic acid, malonic acid, citric acid or lactic acid. This method allows for the tin (II) content to be routinely reduced to below 30 ppm and preferably to below 20 ppm.

In one form of implementation the method for producing the absorbable polyester per this invention involves the use of the following reagents in the extruder:

(a) Hydroxycarboxylic acids in lactone form (b) 1–10%, relative to the total amount of hydroxycarboxylic acids used, of an electrolyte-containing polyol (c) A polymerization catalyst In a particularly preferred form of implementation the method for producing the absorbable polyester according to the invention involves the use of the following reagents in the extruder:

(a) Lactide/glycolide at a ratio of 3:1 to 1:3, preferably 60/40–40/60 and ideally 55/45–45/55

(b) 1–6%, preferably 3–5%, as related to the total monomer amount, of dextran sulfate (c) At least 1000 ppm tin (II), preferably 1000–2000 ppm tin (I), ideally 1200–1600 ppm tin (II), as related to the total monomer amount.

Another object of the invention is constituted of a method for producing the absorbable polyester according to the invention, encompassing the polymerization of hydroxycarboxylic acids, characterized in that the method includes the following consecutive procedural steps:

(a) Mixing of the hydroxycarboxylic acid monomers in the presence of an electrolyte-containing polyol (b) Filling the mixture per (a) into the extruder (c) Adding the catalyst (d) Polymerizing in the extruder A preferred object of this invention is constituted of a method for producing the absorbable polyester per the invention, encompassing the polymerization of lactide and glycolide, characterized in that the method includes the following consecutive procedural steps:

(a) Mixing the lactide and glycolide at a ratio of 60/40–40/60 in the presence of 1–6% DS as related to the total monomer amount (b) Filling the mixture per (a) into the extruder (c) Adding 1000–2000 ppm tin (II)

(d) Polymerizing in the extruder at 170–220° C.

In this form of implementation of the invention the sequence in which the components mixed in step (a) are combined is not critically important. For example, the lactide, glycolide and DS may be filled into the extruder either simultaneously or successively. Alteratively, two or more of the components, for instance the lactide and the DA, may be premixed and the additional component, e.g. the glycolide, may then be added. All of these possible procedural variations are a part and an object of the invention for patent coverage and are subsumed under the expression "mixing of the hydroxycarboxylic acid monomers in the presence of an electrolyte-containing polyol".

The addition, per this invention, of electrolyte-containing polyols and especially of DS in the polymerization in the extruder permits particularly practical and easy control of the properties of absorbable polyesters.

Another object of this invention is therefore constituted of the use of an electrolyte-containing polyol in the production of an absorbable polyester in the extruder.

In a preferred form of implementation, the electrolyte-containing polyol employed in the production of an absorbable polyester in the extruder is DS.

The polyesters according to the invention are particularly suitable for use as matrix polymers for depot formulations of pharmacologically active substances. Examples of such depot formulations include in particular parenteral medications such as microparticles, capsules, implants, powders, granules or pellets, but also inhalational or topical medicaments such as biodegradable wound pads, or PLGA nanospheres for pulmonary application.

One object of this invention is therefore constituted of a pharmaceutical formulation containing a polyester per the invention and at least one pharmacologically active substance.

In this context, the polyester may be in a form where the active substance is embedded (dispersed or dissolved) in the polyester, or the polyester may enclose the active substance, or the polyester may be surface-coated with the active substance.

In a preferred implementation the polyester is in the form of microparticles in which the active substance is embedded. Producing such microparticles is prior-art technology. Popular techniques include for instance coacervation, solvent extraction from an oil-water dispersion, or spray drying.

One object of the invention is therefore constituted of a pharmaceutical formulation containing a polyester per this invention and at least one pharmacologically active substance, with both the polyester and the active substance being in the form of microparticles.

The formulations according to the invention are generally suitable for the administration of pharmacologically active substances. Of particular interest are the formulations for administering biologically active peptides and proteins since these are usually ineffective or inadequately effective when taken orally.

Nonlimiting examples of such peptides include oxytocin; vasopressin; adrenocorticotropic hormone (ACTH); growth factors such as epidermal growth factors (EGF), fibroblast growth factors (a-FGF, b-FGF, FGF-9 etc.), vascular endothelial growth factor (VEGF), tumor necrosis factor (TNF), platelet growth factor (PDGF), neurotrophins (NT 1–3, BDNF, NGF), erythropoietin or insulin-like growth factors (IGF); releasing factors such as luteinic hormone-releasing hormone (LHRH), growth hormone-releasing factor (GRF), gonadotropin-releasing hormone (GnRH), gastrin-releasing factor or tyrosin-releasing hormone (TRH); thyroid-stimulating hormone (TSH); parathyroid hormone (PTH), luteinic hormone (LH); follicle-stimulating hormone (FSH); somatostatin and analogues; somatotropin; gastrin; prolactin; motilin; callicrein; amylin; glucagon; glucagon-like peptide (GLP); calcitonin; calcitonin-related peptide; natriuretic proteins; angiotensins; renin; brandykinin; encephalins; endorphins; interferons (alpha, beta, gamma); chemokins; hematopoietic growth factors such as erythropoietin; stem cell growth factors (SCF), interleukins (e.g. IL-1 to IL-12), granulocyte growth factors (G-CSF and GM-CSF) or monocyte growth factors (M-CSF); peptide antibiotics such as tyrocidin, gramicidin, bacitracin or nisin; angiopeptin; hirudin; thrombopoietin, uroenterones; osteogenic proteins such as the bone morphogenic protein, antibodies and their fragments an derivatives (Fab, (Fab)$_2$, diabodies, scFVs etc.); transcription factors; peptide nucleic acids; vaccine peptides of viral or microbial origin; tumor-based peptides such as PSA, PSMA, PSCA; HLA peptides and MHC antigens; leukocyte markers (e.g. CD3, CD11a–c, CD28, CD30, Cdw52) and their ligands (e.g. B7); T-cell receptors and their fragments; angiostatic peptides such as angiostatin or endostatin; onconase; integrins and integrin-inhibiting peptides (RGDS peptides); lectins such as mistel lectin; calmodulin; vacoactive intestinal peptides (VIP); fertilization-promoting peptides (FFP); cocaine and amphetamine regulated transcript peptides (CART); leptin and its derivatives; soluble receptors; endothelin; insulin; proinsulin and C-peptide as well as their biologically active variants and fragments.

Among these, preference is given to formulations generated in depot form. In this context, the term "depot form" refers to pharmaceutical preparations that release the active substance over a period of at least three days, preferably ten days and ideally 2, 3 or 4 weeks in therapeutically effective quantities.

One particularly preferred peptide is the human proinsulin C-peptide, a 31-amino acid peptide from the proinsulin with a therapeutic effectiveness in the treatment of diabetes and diabetic sequela, as well as its fragments and derivatives as described in the disclosure document WO 98/13384.

Finally, another object of this invention is constituted of a kit comprising a pharmaceutical formulation as described above and a device for administering said formulation. That device may be a syringe or a needleless injection instrument. Appropriate examples have been described in prior art and those skilled in the art are familiar with them.

A kit of that type may also include a device for resuspending the pharmaceutical formulation in cases where the formulation is kept in a dry state and must be dissolved immediately prior to its application or if it must be resuspended.

IMPLEMENTATION EXAMPLES

EXAMPLE #1

Producing a DS Polyester in the Extruder Polymerization

First, the DS is allowed to dry for at least 3 days at room temperature in a medium-high vacuum (about 0.1 mbar).

53 mol % D,L-lactide, 47 mol % glycolide and the predried DS (2 to 4% by weight) are weighed into a mixing barrel. The combination is homogenized for 30 min. in a gyrowheel mixer.

The premixed monomer/DS is placed in a proportioning weigher of the extruder (Leistritz dual-screw extruder model LSM 34 GG) and continuously metered into the extruder via proportioning screws.

A defined quantity of the catalyst, tin (II) 2-ethylhexanoate, is dissolved in toluene and by means of an HPLC pump the catalyst solution is continuously metered into the extruder, at a rate that is so adjusted to the monomer/DS feed rate that the amount of catalyst in the reaction mixture is 1200 ppm.

This is followed by polymerization in the extruder at temperatures between 170 and 220° C.

Processing

The raw polymer is dissolved in acetone overnight. When it is fully dissolved, D,L-lactic acid is added and agitated for another 2–3 hours. The resulting turbid solution (10% by weight polyester in the solvent mixture) is filtered out under light nitrogen pressure.

The filtered polyester solution is precipitated with demineralized water. The polyester precipitate is rinsed, filtered and then dried at a maximum of 35° C. until a constant weight is reached.

EXAMPLE #2

Polyester Analysis

DS polyesters produced as described in Example #1 were analyzed for their chemical composition, their molecular weight and other characteristic values and compared with commercially available PLG standard polymers. The results are shown in the table below:

Glass Transition Temperature (Tg)

The glass transition temperature Tg was determined by differential scanning calorimetry (DSC).

Lactide:Glycolide Ratio

The lactide:glycolide ratio of the copolymers was determined by $^1$H-NMR spectroscopy. 5–20 mg of the substance to be analyzed was dissolved in about 0.6 mL deuterochloroform and $^1$H-NMR spectra were recorded using a 200 MHz spectrometer at a temperature of 25° C. Tetramethylsilane was used for the internal standard. The lactide:glycolide ratio was calculated based on a quantitative determination of the integral of the lactide units (multiplet at around 5.2 ppm) and of the glycolide units (multiplet at around 4.8 ppm).

Determination of the Block Length

The average block length was determined through a $^{13}$C-NMR spectroscopic analysis.

Carbohydrate Content

For a determination of the total carbohydrate concentration in the polymers, the polymers were hydrolized in 12-molar sulfuric acid. The quantitative glucose analysis was performed by anion-exchange chromatographic separa-

| Item Tested | DSS-PLG 3% DSS, (1600 ppm Sn) | DSS-PLG 4% DSS, (1600 ppm Sn) | DSS-PLG 3% DSS (1200 ppm Sn) | Resomer RG502H | Resomer RG503H |
|---|---|---|---|---|---|
| $M_w$ [g/mol] | 17234 | 14137 | 21056 | 8859 | 26151 |
| $M_n$ [g/mol] | 9486 | 7952 | 8493 | 5476 | 11469 |
| PD [$M_w/M_n$] | 1.8 | 1.8 | 2.5 | 1.6 | 2.3 |
| IV [dL/g] | 0.25 | 0.22 | 0.30 | 0.21 | 0.35 |
| $T_g$ [° C.] | 39.6 | 40.5 | 38.9 | 38.0 | 41.0 |
| Lac:Glyc | 53.2:46.8 | 53.1:46.9 | 51.0:49.0 | 52.5:47.5 | 52.2:47.8 |
| Block Length | 3.0 | 3.4 | | | |
| CH Content [ppm] | 13 | 25 | | <det. lim. | <det. lim. |
| Acid Number [mg KOH/g] | 7.9 | 9.0 | 6.7 | 12.6 | 4.2 |
| Water Content [%] | 0.4 | 0.5 | | 0.4 | 0.4 |
| Sulfate Ash [%] | 0.0 | 0.0 | | 0.0 | 0.0 |
| Sn Content [ppm] | 13 | 14 | <10 | 145 | 112 |
| Na Content [ppm] | <5 | <5 | <5 | <5 | <5 |
| S Content [ppm] | <5 | <5 | <5 | <5 | <5 |

$M_w$ = molecular weight (average weight); $M_n$ = molecular weight (average number); PD = polydispersity; IV = inherent viscosity; Lac:Glyc = molecular lactide:glycolide ratio; CH = carbohydrate concentration; Sn = tin; Na = sodium; S = sulfur; det. lim. = detection limit Description of Analytical Methods Determining the Molecular Weight The molecular weight data ($M_w$, $M_n$, PD) were determined by gel permeation chromatography (GPC) on ultrastyragel columns with polystyrene calibration. Tetrahydrofuran (THF) was used for the mobile phase. The detection was made via RI and UV.

Inherent Viscosity (IV)

The inherent viscosity values were determined with a Schott Ubbelohde viscosimeter (per DIN 51562) with a capillary size of 0. The sample solution was a 0.1% polymer-in-chloroform solution. The measuring temperature was 25° C.

tion with subsequent electrochemical detection by comparison against a calibration curve obtained with a glucose reference solution.

Water Content

The water content was determined using a coulometric Karl-Fischer titration after the water was heated to evaporation in the dryer.

Tin, Sodium and Sulfur Content

The tin, sodium and sulfur concentrations were determined by ICP atomic emission spectroscopy after dissolution of the polymers under pressure in a mixture of azotic acid and hydrofluoric acid.

EXAMPLE #3

Removing the Tin (II)

40 kg of the polymer were placed in a 1000 l agitator. 390 l acetone were then added. The polymer was dissolved under constant agitation. This was followed by the addition of 54 kg (45 l) D,L-lactic acid and agitation of the solution for another 2–3 hours.

The solution was prefiltered through a 5 μm filter, pumped into the precipitator (two-component nozzle) and then mixed with demineralized water. After the precipitation the water-acetone mixture was siphoned off and the polymer was washed with water. The polymer was then comminuted at a maximum of 30° C. using an Alexander grinder over a screen and finally desiccated in a filtering dryer.

EXAMPLE #4

Producing the Microparticles 0.55 g of the polymer or polymer mixture was dissolved in glacial acetic acid, 0.045 g of the C-peptide was dissolved in 0.15 ml water and 3.0 ml glacial acetic acid and was slowly blended into the polymer solution. The resulting solution was atomized and dried in a Büchi 190 spray dryer at 60° C. until the microparticles were retrievable in the form of a fine, pourable powder.

EXAMPLE #5

Pharmaceutical Retardant C-Peptide Formulati n 300 mg microparticles containing 22.5 mg C-peptide acetate (Polypeptide Laboratories) were resuspended in 1.5 ml of a solvent (0,9% saline, 0.1% Tween). After vigorous shaking the resulting suspension was ready for application on the patient.

EXAMPLE #6

DS Polyester In-vivo Release Rate as Compared to Lactic Acid-Modified Commercial Polyesters Beagles were subcutaneously given 300 mg microparticles each, loaded with 7.5% C-peptide and based either on DS-modulated polymers or on commercially available standard polymers. At specified times blood samples were taken from the animals and the C-peptide plasma level was quantified using LC-MS. The results are shown in FIGS. 1 and 2.

What is claimed is:

1. An absorbable polyester, obtainable by a process comprising:
   ring-opening polymerizing one or more hydroxycarboxylic acids in lactone form in the presence of an electrolyte-containing polyol,
   wherein polymerizing occurs at a temperature of from 170 to 220° C. and the polyester contains less than about 200 ppm of the electrolyte-containing polyol.

2. The absorbable polyester of claim 1 wherein the polymerizing takes place at a temperature of from 170 to 200° C.

3. The absorbable polyester of claim 1 wherein the polymerizing occurs in the presence of from 1000 to 2000 ppm Sn (II) relative to monomer.

4. The absorbable polyester of claim 1 wherein the polyester has a molecular weight of 7 to 40 kDa.

5. The absorbable polyester of claim 1 wherein the one or more hydroxycarboxylic acids are lactides and/or glycolides.

6. The absorbable polyester of claim 1 wherein the electrolyte-containing polyol is dextran sulfate.

7. The absorbable polyester of claim 6 wherein dextran sulfate is present at a concentration of 1 to 6 percent (w/w) relative to monomer.

8. The absorbable polyester of claim 1 wherein the polyester has an inherent viscosity of 0.25 to 0.45 dl/g (0.1% in chloroform, 25° C.).

9. The absorbable polyester of claim 1 wherein polymerizing occurs within an extruder.

10. The absorbable polyester of claim 1 wherein the process comprises:
    a) mixing the lactone-form one or more hydroxycarboxylic acids with an electrolyte polyol;
    b) introducing the mixture of a) into an extruder;
    c) adding a catalyst to the mixture;
    d) polymerizing in the extruder at a temperature of from 170 to 200° C.

11. The absorbable polyester of claim 1 wherein the polyester is obtained by the process comprising the ring-opening polymerizing.

12. An absorbable polyester, obtainable by a process comprising:
    ring-opening polymerizing one or more hydroxycarboxylic acids in lactone form in the presence of an electrolyte-containing polyol, wherein the polyester contains less than about 200 ppm of the electrolyte-containing polyol.

13. The polyester of claim 12 wherein the one or more hydroxycarboxylic acids are lactides and/or glycolides.

14. The polyester of claim 12 wherein the polyol is dextran sulfate.

15. The polyester of claim 12 wherein polymerizing occurs in an extruder.

16. The polyester of claim 12 wherein the polyester is obtained by the process comprising the ring-opening polymerizing.

17. A method for producing a polyester comprising:
    ring-opening polymerizing one or more hydroxycarboxylic acids in lactone form in the presence of an electrolyte-containing polyol,
    wherein a polyester is produced that contains less than about 200 ppm of the electrolyte-containing polyol.

18. The method of claim 17 wherein the polymerization occurs in an extruder at a temperature of from 170 to 220° C.

19. The method of claim 17 wherein polymerizing occurs in an extruder.

20. The method of claim 17 wherein the method comprises:
    a) mixing the lactone-form one or more hydroxycarboxylic acids with an electrolyte polyol;
    b) introducing the mixture of a) into an extruder;
    c) adding a catalyst to the mixture;
    d) polymerizing in the extruder.

21. The method of claim 20 wherein the catalyst is added at a concentration of at least 1000 ppm relative to the total amount of the hydroxycarboxylic acid monomer.

22. The method of claim 20 wherein in a) the electrolyte-containing polyol is added at a concentration of 1 to 6 percent (w/w) relative to monomer.

23. The method of claim 20 wherein the catalyst content in the polymer is depleted to below 30 ppm.

24. The method of claim 17 further comprising admixing an absorbable polyester produced by the polymerization with a pharmacologically active substance.

25. A pharmaceutical formulation comprising a pharmacologically active substance and a polyester obtainable by a process comprising ring-opening polymerizing one or more hydroxycarboxylic acids in lactone form in the presence of an electrolyte-containing polyol, the polyester containing less than about 200 ppm of the electrolyte-containing polyol.

26. The pharmaceutical formulation of claim 25 wherein the polyester is the form of microparticles.

27. The pharmaceutical formulation of claim 25 wherein the active substance is a peptide.

28. The pharmaceutical formulation of claim 27 wherein the peptide is released in a therapeutically effective quantities over a period of at least two weeks.

* * * * *